US 9,697,481 B2

(12) United States Patent
Charrad et al.

(10) Patent No.: US 9,697,481 B2
(45) Date of Patent: Jul. 4, 2017

(54) METHOD FOR OPERATING A HOSPITAL INFORMATION SYSTEM

(75) Inventors: Chiheb Charrad, Neunkirchen A. Brand (DE); Lutz Dominick, Eggolsheim (DE); Karlheinz Dorn, Kalchreuth (DE); Christian Scharf, Aurachtal (DE); Vladyslav Ukis, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 346 days.

(21) Appl. No.: 12/654,576

(22) Filed: Dec. 23, 2009

(65) Prior Publication Data

US 2011/0153345 A1     Jun. 23, 2011

(51) Int. Cl.
*G06Q 10/00* (2012.01)
*G06Q 10/06* (2012.01)
*G06F 19/00* (2011.01)
*G06Q 50/22* (2012.01)

(52) U.S. Cl.
CPC ........... *G06Q 10/06* (2013.01); *G06F 19/327* (2013.01); *G06Q 10/0633* (2013.01); *G06Q 50/22* (2013.01)

(58) Field of Classification Search
CPC ............................... G06Q 50/22; G06Q 50/24
USPC ........................................................ 705/2, 3
See application file for complete search history.

(56) References Cited

U.S. PATENT DOCUMENTS

| | | | | |
|---|---|---|---|---|
| 5,634,127 A | * | 5/1997 | Cloud et al. | 719/313 |
| 6,253,369 B1 | * | 6/2001 | Cloud | G06F 9/546 |
| | | | | 717/136 |
| 2003/0045958 A1 | * | 3/2003 | Brandt et al. | 700/101 |
| 2003/0191795 A1 | * | 10/2003 | Bernardin et al. | 709/105 |
| 2005/0182657 A1 | * | 8/2005 | Abraham-Fuchs et al. | 705/2 |
| 2006/0070025 A1 | * | 3/2006 | Mauceri et al. | 717/106 |
| 2006/0282291 A1 | * | 12/2006 | Runciman | 705/3 |
| 2007/0050759 A1 | * | 3/2007 | Boing et al. | 717/135 |
| 2010/0287280 A1 | * | 11/2010 | Sivan | 709/226 |

OTHER PUBLICATIONS

Minmin Han, "Managing Exceptions in the Medical Workflow Systems," May 28, 2006, pp. 741-750.*

* cited by examiner

*Primary Examiner* — Lena Najarian
(74) *Attorney, Agent, or Firm* — Harness, Dickey & Pierce, P.L.C.

(57) ABSTRACT

A method of operating a hospital information system, and a hospital information system are disclosed. In at least one embodiment, the method includes providing a taskflow editing tool with a limited number of editing options to a user; creating a taskflow defining a number of tasks and connections of the tasks by the user using the taskflow editing tool; and performing an automated test run of the created taskflow, wherein the automated test run is checked according to a number of criteria and wherein results of the check are reported to the user.

10 Claims, 1 Drawing Sheet

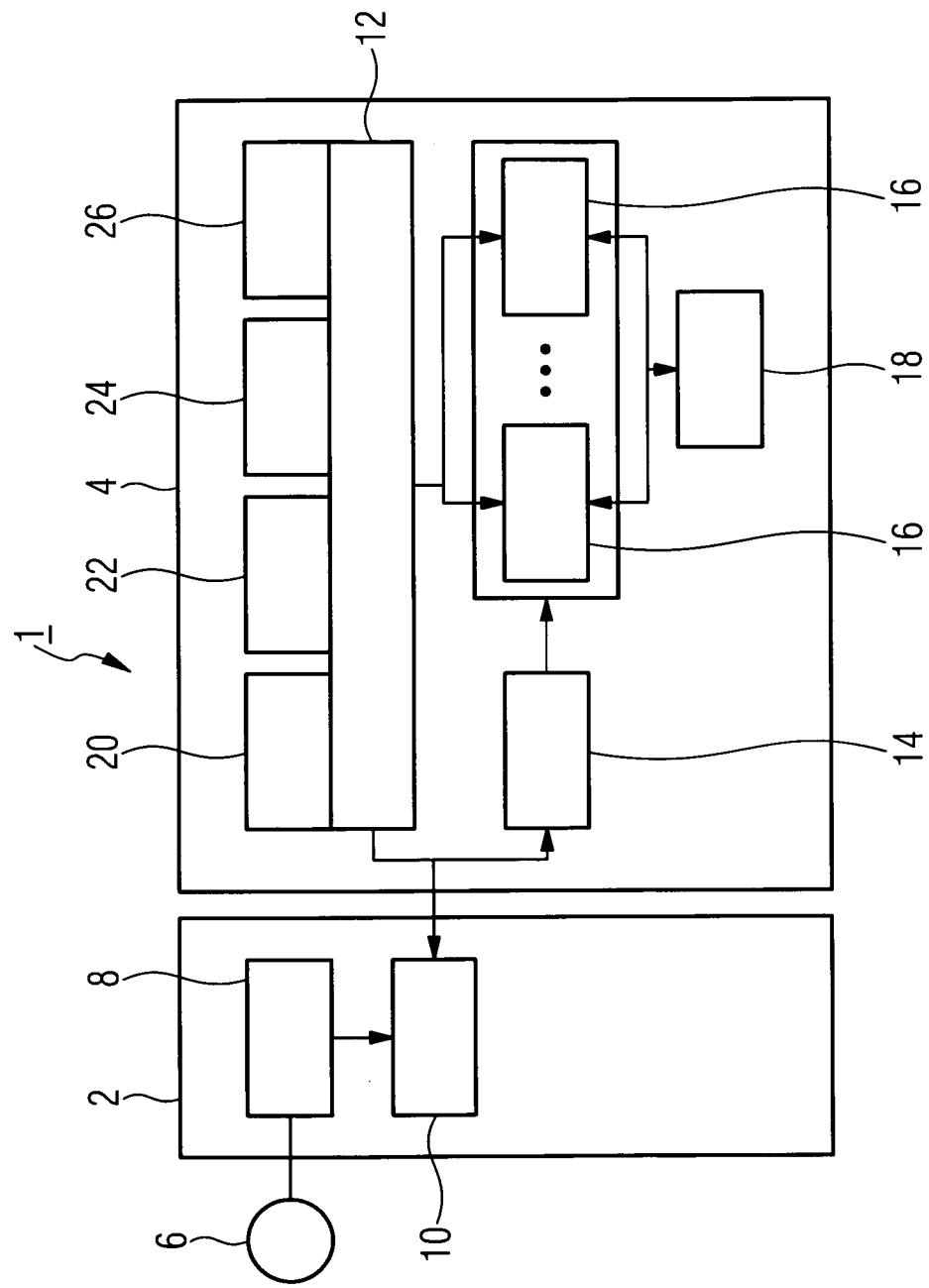

METHOD FOR OPERATING A HOSPITAL INFORMATION SYSTEM

FIELD

At least one embodiment of the present invention generally relates to hospital information systems, and in particular to a method for operating a hospital information system wherein taskflows comprising a number of tasks and their connections defining certain operational procedures within a hospital environment are provided.

BACKGROUND

A hospital information system is a comprehensive, integrated information system designed to manage the administrative, financial and clinical aspects of a hospital or other medical installations. These hospital information systems are usually based on a network of server and client machines and help to organize the medical treatment comprising diagnostic tasks such as radiology or other examinations as well as treatment tasks. In order to organize and optimize the operational procedures within a hospital environment, a hospital information system usually provides workflows or taskflows defining a number of tasks and their connections in order to schedule, for example, the treatment of a patient and coordinate the clinical processes. The organization of these worksteps into information technology based taskflow helps to optimize the treatment of a patient and the efficiency in a hospital environment.

During creation of a taskflow a high number of boundary conditions have to be taken into account: the taskflows have to be adjusted to the resources available in each specific hospital environment to avoid resource conflicts and, for example, a possible loss of data during the execution of the taskflow. Furthermore, since in a clinical environment these taskflows relate to the treatment of human individuals, a high level of fail-safety and integrity has to be maintained at all times, because errors in the taskflow may put a patient in harm's way.

To achieve this high level of safety and integrity, these taskflows are therefore usually created by approved personnel chosen by the manufacturer of the hospital information system. This guarantees that the manufacturer of the hospital information system can ensure the quality of each taskflow. If new taskflows are to be integrated into an existing hospital information system, the manufacturer is usually instructed accordingly and these new taskflows are then created by the manufacturer and introduced into the hospital information system with an upgrade at a later time.

SUMMARY

Due to the above requirements, the inventors have recognized that hospital information systems therefore lack flexibility regarding the creation of new taskflows or modifications to existing taskflows directly in the hospital environment. Since every update or upgrade of the hospital information system has to be approved by the manufacturer to ensure fail-safety and integrity, modifications to an existing system usually take a long time to be installed on site.

Accordingly, in at least one embodiment, a method of operating the hospital information system is provided that allows the user of a hospital information system to modify, create, store, execute, copy and relay taskflows during normal operation quickly and safely.

At least one embodiment of the present invention provides a method of operating a hospital information system that ensures the fail-safety and integrity of the created taskflows without the need of intervention by the manufacturer of the hospital information system.

at least one embodiment of the present invention provides an improved method of operating a hospital information system which guaranties a good performance and the optimal use of resources by the taskflows created in the hospital environment.

To the accomplishment of the foregoing and related ends, the invention then comprises the features hereinafter fully described and particularly pointed out in the claims, the following description and drawing setting forth in detail certain illustrative embodiments of the invention, these being indicative, however, of but several of the various ways in which the principles of the invention may be employed.

BRIEF DESCRIPTION OF THE DRAWING

The above brief description as well as further objects, features and advantages of the present invention will be more fully appreciated by referring to the following description of a presently preferred but nonetheless illustrative embodiment in accordance with the present invention when taken in connection with a sole FIGURE of the accompanying drawing, The FIGURE is a schematic diagram illustrating a client machine and a server machine of a hospital information system.

DETAILED DESCRIPTION OF THE EXAMPLE EMBODIMENT

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Referring to the drawing, the FIGURE shows a part of a hospital information system 1 comprising a client machine 2 and a server machine 4. The hospital information system 1 is an integrated system providing a number of taskflows comprising a number of tasks and their connections defining and organizing operational processes in the hospital environment. This is achieved by providing the required information to the specific client machine 2 within the hospital and connecting the collected information between the different users in the hospital environment.

In order to allow the creation and modification of such taskflows within the hospital environment without the need for the manufacturer of the hospital information system 1 to intervene, a user 6 who wishes to create or modify a taskflow is provided a taskflow editing tool 8 that allows such creation and modification of taskflows. Compared to the possibilities of the manufacturer concerning the manipulation of the data structure of the taskflows, the taskflow editing tool 8 provided to the user 6 has a limited, predefined number of editing options. The scope of these editing options may be adjusted to safety and integrity policies of the manufacturer, the specific legislation or certain hospital policies.

The user 6 then creates a user-defined taskflow 10 by means of the taskflow editing tool 8 by defining tasks and their connections etc. During the editing of taskflow 10 by the user 6 as well after completion of all modifications, a control module 12 is automatically activated and takes control of the taskflow module 14. Then, by means of the control module 12 an automated test run of the user-defined taskflow 10 is performed by executing the tasks 16 and checking this test run according to a number of criteria predefined in a control module 12. The results of this test run are then reported by the control module 12 to the user 6 which allows the user to react to possible errors and problems emerging during the test run by modifying the creative taskflow 10 accordingly.

Preferably, the test run performed by the control module 12 is conducted without any interaction with the user 6, such that the user 6 has no possibility to interfere with the test run progress that is crucial to ensure the safety and integrity of the created taskflow 10.

As shown in the FIGURE, the hospital information system 1 comprises a server machine 4 and a client machine 2 and the taskflow is created by the user 6 on the client machine 2, implying that the taskflow editing tool 8 preferably runs on the client machine 2. The test run performed by the control module 12, however, is preferably completely run on the server machine 4, which means that only the back ends of each task 16 have to be started. The front ends that correspond to the user interaction part of each task 16, usually run on client machines within the hospital environment corresponding to client machine 2. These front ends may be started as well by the control module 12 during the test run, however this is not necessary. Where input data for the execution of a certain task 16 is needed to perform the test run, anonymous input data 18 is used during the test run.

During the execution of the task 16 in the test run, the control module 12 checks the test run according to a number of predefined criteria. Preferably, these criteria comprise the executability of the taskflow 10 on the technical resources provided by the hospital information system 1. By means of information technology and resource strategies 20, the control module 12 is able to recognize if modifications relating to the information technology integration are necessary and whether resource shortages are to be expected during execution of the created taskflow 10. This test regarding the integrability of the taskflow 10 and the task 16 into the given information technology infrastructure includes both local and remote services such as the availability of enterprise services.

The preset criteria checked by the control module 12 further preferably comprise the conformity of the taskflow 10 with a communication protocol of the tasks 16 and/or their connections. To this end, the control module 12 has communication strategies 22 in order to recognize which corrections and modifications concerning the task communication are necessary and where certain configurations have to be added. By means of these configurable communication strategies 22, the taskflow 10 is provided with the anonymized input data 18 and the tasks 16 are provided with action commands in a particularly flexible, automated and adaptable way. In a similar manner, the output data created during the tast run of the taskflow 10 is evaluated specifically to both tasks and taskflows, wherein task specifical strategies can be configured within the control module 12.

The preset criteria checked during the test run furthermore preferably comprise the compliance of the taskflow 10 with a predefined performance criterion. The control module 12 is able to predict and/or measure and evaluate, whether the chosen connection between the tasks 16 yields the optimal performance during execution of the task flow 10. This may also include quality of service features such as scalability, performance, availability or limitations due to few or suboptimal licenses which may be automatically determined or at least predicted with data measured during the test run of taskflow 10 and accordant evaluation strategies.

Furthermore, the preset criteria checked during the test run preferably comprise the compliance of the taskflow 10 with a predefined risk and/or safety criterion. During the test run of the task flow 10, the control module 12 checks for risks that emerge or are to be expected and may therefore evaluate the risk potential of, the creative taskflow 10 by means of configurable security and risk strategies 24. The evaluated risk potential is then reported to the user 6.

Furthermore, the result of the check regarding the predefined risk and/or safety criterion is preferably stored with the task flow. For example, the control module 12 may determine a configurable maturity level of the taskflow 10 and can store this maturity level with the created taskflow 10 in form of a certificate. This certificate then allows an immediate evaluation of the created taskflow 10 for other users within the hospital environment and may also help in the decision whether to use this created taskflow 10 before or after consultation of the manufacturer or further non-automated manual tests.

Preferably, the control module 12 has improvement and error strategies 26 comprising a number of predefined improvement and/or problem solution modifications, by which means the control module 12 may chose a subset from these modifications on the basis of the results of the check in the test run. The chosen improvements or error solutions may then be reported to the user 6. Preferably, these modifications are automatically integrated by the control module 12 into the created taskflow 10, thus automatically improving and solving problems occurring during the test run of the taskflow 10 and optimizing the taskflow 10 in view of the predefined checked criteria. This means that for each task 16 the control module 12 intercepts occurring errors, evaluates these errors by means of the improvement and error strategies 26 and chooses a configurable and situation-specific solution action. If configured, the control module 12 automatically executes this solution action and in any case reports the solution action to the user 6.

The control module 12 can further recognize by way of configurable strategies whether the task flow 10 can be started and stopped, which means whether an intermediate state of the taskflow 10 may be suspended and afterwards resumed and whether the taskflow complies to domain-specific and configurable protocols regarding the communication strategies between tasks 16 (e.g. a "findings protocol") or between a task 16 and the taskflow module 14 (e.g. a "detached protocol").

In a hospital environment, the tasks 16 are physically executed by medical personnel. For a simple management of the authorizations of the specific personnel, tasks are therefore supplied with so-called roles that define a certain scope of authorizations that are required to execute the specific task 16. The control module 12, during the test run of the taskflow 10 can also check whether the proper role has been supplied to the specific task 16 created in the taskflow 10 and may add the required roles during the test run if errors occur during execution of the taskflow 10. Therefore, it is also possible that a user 6 creates a taskflow 10 requiring roles that the user himself does not possess. Since the control module 12 can work with several roles and authorizations, this allows a specifically flexible creation of taskflows 10 in the hospital environment.

Due to the resource strategies 20 of the control module 12, which measures the resource usage by the taskflow 10 and the tasks 16 and the required availability of hardware and special hardware, the optimization strategies 26 also include possibilities to optimize resource usages and optimization of the connections between the tasks 16.

Advantages of the invention should now be apparent. In particular, the invention permits the creation of taskflows within the hospital environment and without interaction with the manufacturer of the hospital information system. The created taskflows are automatically checked according to a set of predefined criteria regarding safety, quality of service and hospital policies. The evaluation of the created taskflow is done live and online. Since the test run is performed by the control module 12 without interaction with the user, the technical dimensions of the newly created taskflow do not have to be known by the user, who is usually a physician, rather the user may only be concerned with the medical aspects of the created taskflow while the technical aspects are handled by the control module 12. If errors occur during the test run, the user is only provided with valid solutions or an automatic solution is applied by the control module 12.

The control module 12 in a way takes the role of the manufacturer during the creation of a taskflow and conducts a flexible and adapted quality assurance on site within the hospital environment. This also allows the users to exchange created taskflows with each other, also beyond the boundaries of the specific department or hospital, since the control module 12 works independently of the specific taskflow, user 6 and environment and automatically works with the adapted taskflow in the new environment, whereby it is recognized whether certain tasks are not yet implemented in the destination environment or if a wrong software solution is installed. In summary, the method and apparatus according to the invention provides for a particularly flexible and adaptable way of creating taskflows within the hospital environment.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

REFERENCE NUMERALS 1 hospital information system
2 client machine
4 server machine
6 user
8 taskflow editing tool
10 user-defined taskflow
12 control module
14 taskflow module
16 task
18 anonymous input data 20 IT and resource strategies
22 communication strategies
24 security and risk strategies
26 improvement and error strategies The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of operating a hospital information system that includes a client machine running a front end of a user-defined taskflow and a server machine running a back end of the user-defined taskflow, the user-defined taskflow defining operational procedures to diagnose and treat patients within a hospital environment, comprising:

providing, by the hospital information system, a taskflow editing tool with a limited number of editing options to a user of the hospital information system;

creating, by the client machine of the hospital information system, the user-defined taskflow defining a plurality of tasks associated with diagnostics and treatment and connections between each of the plurality of tasks;

performing, by the hospital information system, an automated test run completely on the server machine by running the back end of each task of the user-defined taskflow on the server machine without running the front end of the user-defined taskflow on the client machine such that the user-defined taskflow is completely run on the server machine without interaction with the user, wherein performing the automated test run completely on the server machine includes, executing the plurality of tasks of the user-defined taskflow on the server machine during the automated test run, inputting anonymous data during the automated test run for each task of the user-defined taskflow that requires input data, checking if modifications relating to information technology integration are necessary and whether resource shortages are expected during execution of the plurality of tasks of the user-defined taskflow based on the execution of the test run of the plurality of tasks, reporting results of the checking of the executed plurality of tasks in the automated test run to the user, and automatically modifying the user-defined taskflow based on the results of the checking such that the modified user-defined taskflow integrates the information technology and avoids the resource shortages; and running, by the hospital information system, the modified user-defined taskflow such that the back end of each task of the modified user-defined taskflow is run on the server machine and the front end of each task of the modified user-defined taskflow is run on the client machine.

2. The method of claim 1, wherein the checking includes checking the executability of the user-defined taskflow on one or more technical resources provided by the hospital information system.

3. The method of claim 2, wherein the checking includes checking the conformity of the user-defined taskflow with a communication protocol of at least one of the task and the connection.

4. The method of claim 3, wherein the checking includes checking the compliance of the user-defined taskflow with a performance criterion.

5. The method of claim 4, wherein the checking includes checking the compliance of the user-defined taskflow with at least one of a risk and safety criterion.

6. The method of claim 5, wherein the results of the automated test run regarding the at least one of risk and safety criterion is stored with the user-defined taskflow.

7. The method of claim 1, further comprising:
choosing a subset from a number of at least one of improvement and problem solution modifications on the basis of the results of the automated test run, wherein the subset is reported to the user.

8. The method of claim 6, further comprising:
automated modification of the user-defined taskflow according to the chosen subset of the at least one of improvement and problem solution modifications.

9. A hospital information system that includes a client machine running a front end of a user-defined taskflow and a server machine running a back end of the user-defined taskflow, comprising:
a client machine configured to create the user-defined taskflow defining a plurality of tasks associated with diagnostics and treatment and connections between each of the plurality of tasks by the user using a taskflow editing tool with a limited number of editing options provided to a user; and
a server machine configured to perform an automated test run completely on the server machine by running the back end of each task of the user-defined taskflow on the server machine without running the front end of the user-defined taskflow on the client machine such that the user-defined taskflow is completely run on the server machine without interaction with the user, wherein performing the automated test run completely on the server machine includes,
executing the plurality of tasks of the user-defined taskflow on the server machine during the automated test run,
inputting anonymous data during the automated test run for each task of the user-defined taskflow that requires input data,
checking if modifications relating to information technology integration are necessary and whether resource shortages are expected during the execution of the plurality of tasks of the user-defined taskflow based on the execution of the test run of the plurality of tasks,
reporting results of the checking of the executed plurality of tasks in the automated test run to the user, and
automatically modifying the user-defined taskflow based on the results of the checking such that the modified user-defined taskflow integrates the information technology and avoids the resource shortages; and wherein the hospital information system is configured to run the modified user-defined taskflow such that the back end of each task of the modified user-defined taskflow is run on the server machine and the front end of each task of the modified user-defined taskflow is run on the client machine.

10. A non-transitory computer readable medium including program segments for, when executed on a hospital information system that includes a client machine running a front end of a user-defined taskflow and a server machine running a back end of the user-defined taskflow, causing the hospital information system to:
provide a taskflow editing tool with a limited number of editing options to a user of the client machine;
create the user-defined taskflow defining a plurality of tasks associated with diagnostics and treatment and connections between each of the plurality of tasks;
perform an automated test run completely on the server machine by running the back end of each task of the user-defined taskflow on the server machine without running the front end of the user-defined taskflow on the client machine such that the user-defined taskflow is completely run on the server machine without interaction with the user, wherein performing the automated test run completely on the server machine includes,
executing the plurality of tasks of the user-defined taskflow on the server machine during the automated test run,
inputting anonymous data during the automated test run for each task of the user-defined taskflow that requires input data,
checking if modifications relating to information technology integration are necessary and whether resource shortages are expected during the execution of the plurality of tasks of the user-defined taskflow based on the execution of the test run of the plurality of tasks,
reporting results of the checking of the executed plurality of tasks in the automated test run to the user, and
automatically modifying the user-defined taskflow based on the results of the checking such that the modified user-defined taskflow integrates the information technology and avoids the resource shortages; and
run, by the hospital information system, the modified user-defined taskflow such that the back end of each task of the modified user-defined taskflow is run on the server machine and the front end of each task of the modified user-defined taskflow is run on the client machine.

* * * * *